US00PP29492P2

(12) United States Plant Patent
de Ruyver

(10) Patent No.: US PP29,492 P2
(45) Date of Patent: Jul. 10, 2018

(54) ***LAVANDULA* PLANT NAMED 'RUYLAA1701'**

(50) Latin Name: *Lavandula angustifolia*
Varietal Denomination: RUYLAA1701

(71) Applicant: Kurt de Ruyver, Oudenaarde (BE)

(72) Inventor: Kurt de Ruyver, Oudenaarde (BE)

( * ) Notice: Subject to any disclaimer, the term of this patent is extended or adjusted under 35 U.S.C. 154(b) by 0 days.

(21) Appl. No.: 15/731,803

(22) Filed: Aug. 3, 2017

(51) Int. Cl.
*A01H 5/02* (2018.01)

(52) U.S. Cl.
USPC ..... Plt./445

(58) Field of Classification Search
USPC ..... Plt./445
See application file for complete search history.

*Primary Examiner* — Annette H Para
(74) *Attorney, Agent, or Firm* — Samuel R. McCoy, Jr.

(57) ABSTRACT

'RUYLAA1701' is a new and distinctive variety of *Lavandula* which is characterized by a relatively compact growth habit, a broad obovate plant form, pubescent greyed-green foliage, an abundance of dark violet-blue labiate flowers borne on terminal spike inflorescences, and continuous flowering with no vernalization requirement. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Lavandula angustifolia.*

Variety denomination: The inventive variety of *Lavandula* disclosed herein has been given the variety denomination 'RUYLAA1701'.

BACKGROUND OF THE INVENTION

Parentage: 'RUYLAA1701' is a seedling selection resulting from the controlled pollination of *Lavandula angustifolia* 'Dwarf Blue' (not patented), the seed parent, with an unnamed *Lavandula multifida* plant (not patented), the pollen parent, at a commercial nursery in Oudenaarde, Belgium, in July of 2014. 'Dwarf Blue' was selected as the seed parent due to its compact growth habit and dark purple flowers, while *Lavandula multifida* was selected as the pollen parent due to its short time to flower from cuttings and no vernalization requirement. The objective of the breeding program was to select a cultivar or cultivars with a relatively compact growth habit, a short time to flower, and dark violet-blue flowers. In May of 2015, one candidate plant was observed to exhibit this unique combination of traits and, in June of 2015, the inventor selected the new *Lavandula* cultivar 'RUYLAA1701' for commercial introduction.

Asexual Reproduction: Asexual reproduction of 'RUYLAA1701' was first accomplished in September of 2015 by rooting softwood stem cuttings at a commercial greenhouse in Heythuysen, Netherlands. Two successive generations have shown that the unique features of the instant cultivar are stable and reproduce true to type.

SUMMARY OF THE INVENTION

The cultivar 'RUYLAA1701' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Lavandula* cultivar, 'RUYLAA1701'.

1. *Lavandula* 'RUYLAA1701' exhibits a relatively compact growth habit and a broad obovate plant form; and
2. *Lavandula* 'RUYLAA1701' exhibits pubescent greyed-green foliage; and
3. *Lavandula* 'RUYLAA1701' exhibits an abundance of dark violet-blue labiate flowers borne on terminal spike inflorescences; and
4. *Lavandula* 'RUYLAA1701' exhibits continuous flowering without no vernalization requirement.

BOTANICAL DESCRIPTION OF THE PLANT

Figure 1:
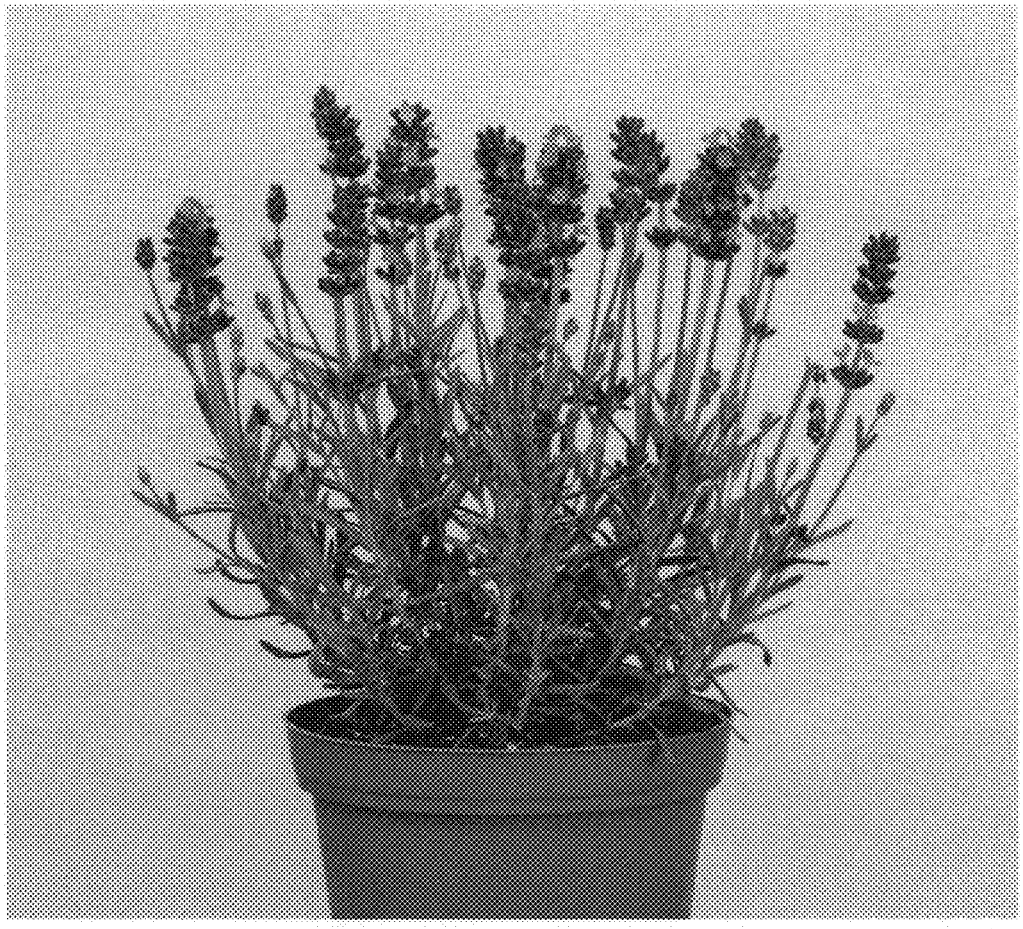
FIG. 1 shows, as nearly true as it is reasonably possible to make the same in color illustrations of this type, an exemplary 'RUYLAA1701' plant at approximately 6 month old, potted into a 13 cm nursery pot, grown in a greenhouse in Oudenaarde, Belgium.
Figure 2:
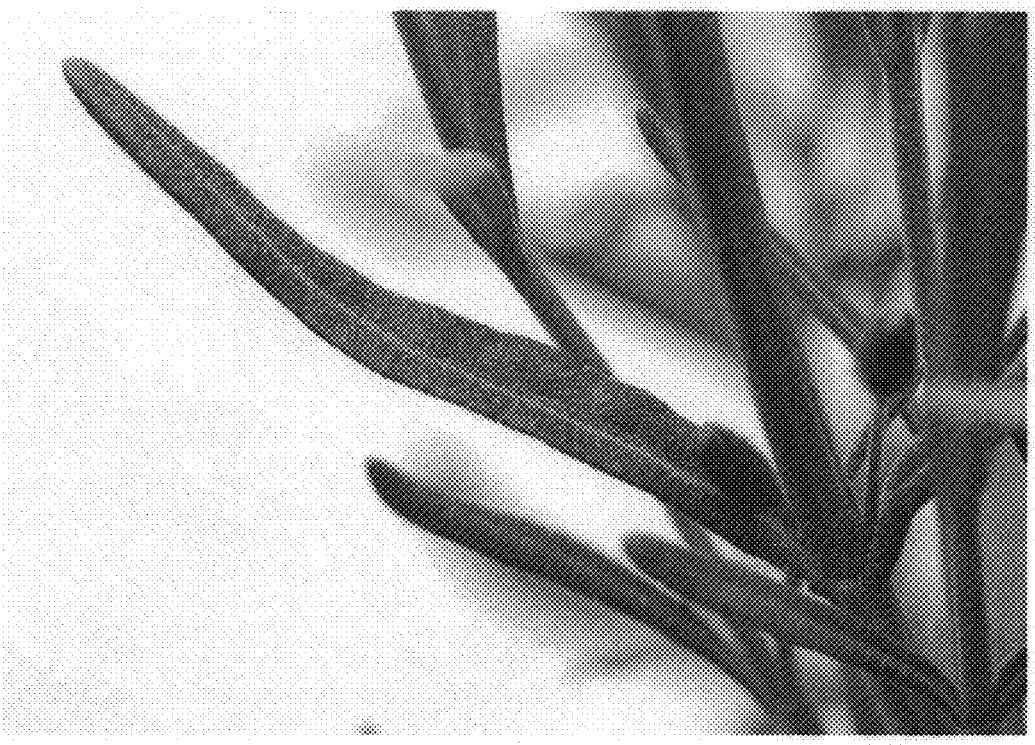
FIG. 2 shows, as nearly true as it is reasonably possible to make the same in color illustrations of this type, the typical foliage of the plant in FIG. 1.
Figure 3:
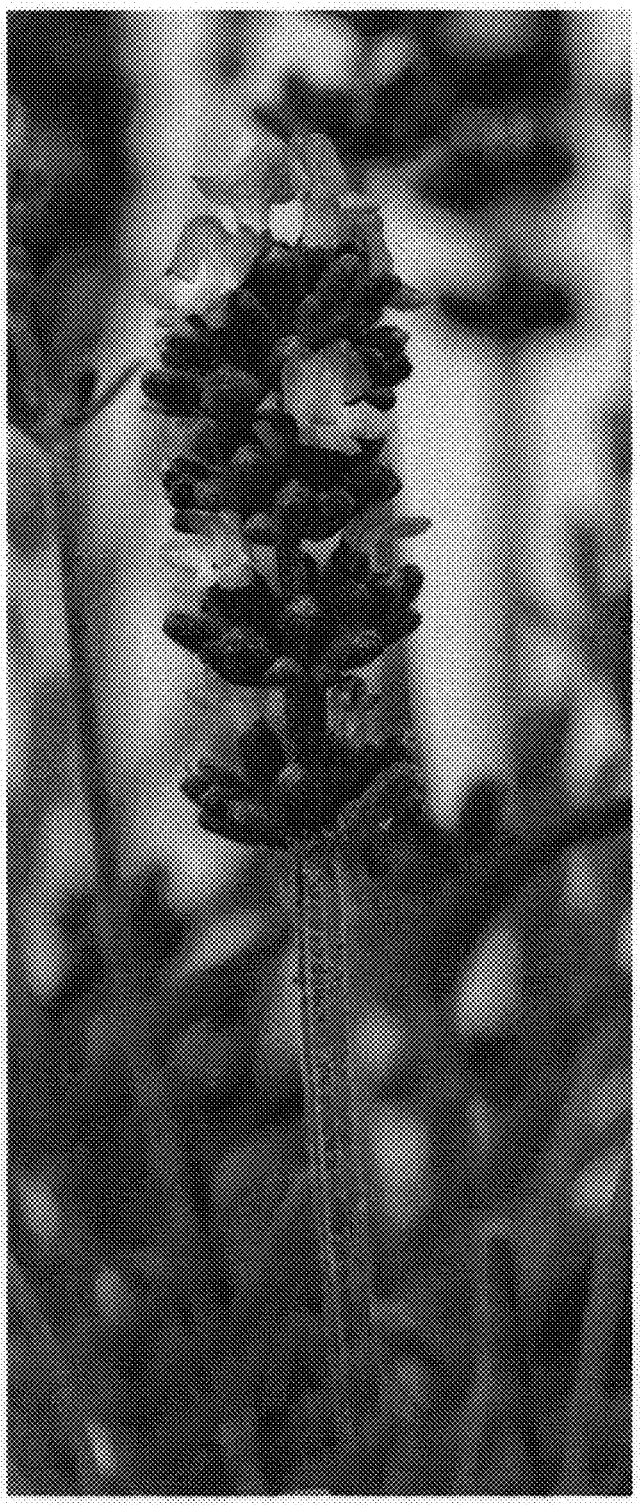
FIG. 3 shows, as nearly true as it is reasonably possible to make the same in color illustrations of this type, the typical inflorescence of the plant in FIG. 1.

The following is a detailed botanical description of a new and distinct variety of *Lavandula* known as 'RUYLAA1701', based upon observations of 6 month old greenhouse-grown plants in 13 cm nursery containers, produced in Oudenaarde, Belgium. Plants were grown using conventional greenhouse production protocols for *Lavandula* plants which consisted of flood bench irrigation, as well as fertigation applications. No pest or disease control measures were utilized in production. Plants were produced with full sun exposure and no photoperiodic treatments or artificial light was given to the plants. Observation data was recorded in June of 2017.

Those skilled in the art will appreciate that certain characteristics will vary with older or, conversely, with younger plants. 'RUYLAA1701' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'RUYLAA1701' and comparisons with the parent and most similar variety of common knowledge are provided below.

General plant description:

*Growth habit*.—A broad, spreading to upright perennial subshrub.

*Plant form*.—Broad obovate.

*Height*.—13.7 cm to the top of the foliar plane; 19.2 cm to the top of the floral plane.

*Spread*.—22.7 cm.

*Plant vigor*.—Low to moderate.

*Growth rate*.—Moderate.

*Propagation*.—Softwood stem cuttings; rooting is initiated in approximately 14 days when grown in a greenhouse with an ambient average temperature of 18 degrees Celsius.

*Time to produce a finished plant*.—Approximately 12 weeks are required to produce a marketable finished plant in a 13 cm pot.

*Pest resistance and susceptibility*.—Not any more or less tolerant or susceptible to pests or diseases known to effect *Lavandula*.

*Environmental tolerances*.—Adapt to, at least, USDA Zones 6 to 10 and temperatures ranging from at least minus 17 degrees Celsius to 40 degrees Celsius; moderate tolerance to rain; high tolerance to wind.

Root system: Dense fibrous root system; relatively shallow; color of juvenile roots is nearest to yellow-white, RHS 158B; older roots are greyed-orange, RHS 163C.

Stem:

*Branching habit*.—Basally branching main stems; freely branching with lateral branches. Stems and branches are strongly aromatic, typical of *Lavandula angustifolia*. Pinching isn't required but will improve branching.

*Number of primary (main) stems per plant*.—28.

*Main stem length*.—8.4 cm.

*Main stem diameter*.—0.2 cm.

*Main stem internode length*.—1.6 cm.

*Number of secondary (lateral) branches per plant*.—60.

*Appearance and shape*.—Quadrangular.

*Aspect*.—70 degrees from vertical, on average; varying between 50 and 90 degrees.

*Luster*.—Matte, due to the dense woolly pubescence.

*Strength*.—Moderately strong.

*Color, juvenile*.—Yellow-green, nearest RHS 144B.

*Color, mature*.—Yellow-green, nearest to in between RHS 145B and 145C.

*Color of oldest stems*.—Grey-brown, nearest to RHS 199B.

*Color at internodes*.—Yellow-green, nearest to in between RHS 145B and 145C.

*Pubescence*.—Tomentose; average length of hairs is 0.02 cm and colored green-white; hairs are so minute that it is impossible to accurately assign an R.H.S. color designation.

Foliage:

*Arrangement*.—Opposite.

*Attachment*.—Sessile.

*Division*.—Simple.

*Attitude*.—Upward; apex occasionally curled upward or downward.

*Quantity*.—Average of 12 leaves per lateral branch.

*Fragrance*.—Strongly aromatic, typical of *Lavandula angustifolia*.

*Lamina*.—Dimensions — 3.5 cm long and 0.5 cm wide, on average. Shape — Narrow oblanceolate. Aspect — Slightly carinate; revolute. Apex — Obtuse. Base — Broad cuneate. Margin — Entire; not undulated. Pubescence of adaxial surface — Moderately woolly pubescent; average length of hairs is 0.02 cm and colored green-white; hairs are so minute that it is impossible to accurately assign an R.H.S. color designation. Pubescence of abaxial surface — Moderately woolly pubescent; average length of hairs is 0.02 cm and colored green-white; hairs are so minute that it is impossible to accurately assign an R.H.S. color designation. Luster of adaxial surface — Matte. Luster of abaxial surface — Matte. Color — Juvenile foliage, adaxial surface — Green, nearest to RHS 137B. Juvenile foliage, abaxial surface — Green, nearest to RHS 137D. Mature foliage, adaxial surface — Green, nearest to RHS NN137C. Mature foliage, abaxial surface — Green, nearest to in between RHS 137B and 137C. Venation — Pattern — Pinnate. Venation color, adaxial surface — Yellow-green, nearest to RHS 146A. Venation color, abaxial surface — Yellow-green, nearest to RHS 147A, and margined green, nearest to RHS 143C.

Inflorescence:

*Type*.—Terminal spike.

*Natural flowering season*.—Late spring through late summer in Oudenaarde, Belgium.

*Time to flower*.—Approximately 13 weeks.

*Dimensions*.—3.9 cm high, not including peduncle, and 1.9 cm in diameter.

*Abundance of inflorescence*.—Very abundant.

*Quantity of open flowers and buds per inflorescence*.—110 flowers.

*Quantity of open flowers per plant*.—Approximately 320.

*Quantity of buds per plants*.—Approximately 4,000.

*Attitude*.—Upright.

*Peduncles*.—Length — Average of 8.0 cm. Diameter — Average of 0.2 cm. Attitude — Upright. Strength — Strong. Texture — Moderately woolly pubescent; average length of hairs is 0.02 cm and colored green-white; hairs are so minute that it is impossible to accurately assign an R.H.S. color designation. Luster — Matte. Color — Green, RHS 138B.

Flower buds:

*Shape*.—Narrow ovate.

*Length*.—Average of 0.5 cm.

*Diameter*.—Average of 0.3 cm.

*Texture*.—Densely woolly pubescent; average length of hairs is 0.05 cm and colored violet, nearest to RHS 86A.

*Luster*.—Matte.

*Color*.—Yellow-green, nearest to RHS 147A, with pubescence removed; apex is violet-blue, RHS 93B.

Flower:

*Flowering habit*.—Moderately freely flowering.

*Form*.—Salverform; petals fused into one upper lip which is split into two identical petal lobes, and one lower lip which is split into three identical petal lobes.

*Flower vertical height*.—0.8 cm.

*Flower diameter*.—0.75 cm.

*Flower length*.—1.0 cm.

*Floral throat diameter*.—0.2 cm.

*Floral throat texture*.—Glabrous; smooth.

*Diameter of floral tube*.—0.2 cm.

*Length of floral tube*.—0.7 cm.

*Floral tube texture*.—Outer side is moderately pubescent with a very short tomentose pubescence; average length of hairs is approximately 0.02 cm and colored white; hairs are so minute that it is impossible to accurately assign an R.H.S. color designation.

*Aspect*.—Flowers are outward facing.

*Fragrance*.—Non-fragrant.

*Lastingness*.—Approximately 4 weeks.

*Persistent*.—Self-cleaning.

*Pedicels*.—Dimensions — 0.175 cm long and 0.075 cm in diameter. Aspect — Upward; approximately 50 degrees to the peduncle axis. Strength — Moderately strong. Texture — Moderately woolly pubescent; average length of hairs is 0.02 cm and colored green-white; hairs are so minute that it is impossible to accurately assign an R.H.S. color designation. Luster — Matte. Color — Yellow-green, RHS 147A.

*Petals*.—Quantity of Petals — 2. Arrangement — Labiate; one upper lip and one lower lip which are fused at the proximal half of the petals. Shape of petal lobes — Upper and lower petal lobes are spatulate. Dimensions, free portion of the upper petal — 1.1 cm long and 0.45 cm wide. Dimensions, free portion of the lower petal — 0.95 cm long and 0.2 cm wide. Apex — Both the upper and lower petal lobes are obtuse. Base — Fused into a tube. Margin — All petal lobs with entire margins which are slightly undulated. Aspect — Slightly curled upward at the apex of the lobes. Texture and luster of upper surface — Velvety; matte. Texture and luster of lower surface — Moderately velvety; matte. Petal color when opening, upper surface — Violet-blue, nearest to in between RHS N89D and 93B. Petal color when opening, lower surface — Violet-blue, nearest to RHS N89D. Petal color when fully opened, upper surface — Violet-blue, nearest to RHS 92A. Petal color when fully opened, lower surface — Violet-blue, nearest to RHS 90D. Petal venation — No venation is visible. Floral throat color — Violet-blue, nearest to RHS 91C. Floral throat venation color — No venation is visible. Corolla tube color, when fully opened — Violet, RHS N88D, and fading white towards the base, RHS NN155D. Floral tube venation color — No venation is visible.

*Calyx*.—Shape — Campanulate. Length — 0.5 cm. Diameter — 0.075 cm. Sepals — Length — 1.1 cm. Width — 0.6 cm, but folded so appears narrower. Arrangement — Fused into a campanulate shape. Quantity — 5. Shape — Linear; fused into a campanulate shape. Apex — Obtuse. Base — Fused; only the distal 5 percent is free. Sepal lobe margin — Entire; not undulated. Texture and luster, upper surface — Glabrous, smooth; matte. Texture and luster, lower surface — Densely woolly pubescent; average length of hairs is 0.05 cm and colored violet, nearest to RHS 86A; matte. Color when opening, upper surface — Green, RHS 143C. Color when opening, lower surface — Yellow-green, nearest to RHS 147A with pubescence removed. Color when fully opened, upper surface — Green, RHS 143C. Color when fully opened, lower surface — Yellow-green, nearest to RHS 147B with pubescence removed.

Reproductive organs:

*Stamens*.—Quantity — 4. Anthers — Attachment — Dorsifixed. Shape — Short kidney-shaped. Dimensions — Approximately 0.05 cm long and 0.05 cm wide. Color — Brown, nearest to RHS 200A. Filaments — Length — 0.15 cm, on average. Color — White, nearest to RHS NN155D. Pollen, amount — Moderately abundant. Pollen color — Yellow-orange, nearest to RHS 17B.

*Pistil*.—Quantity — 1. Length — 0.5 cm. Style — Length — 0.425 cm. Color — Green-white, nearest to RHS 157D. Stigma — Shape — Club-shaped. Length — 0.075 cm. Diameter — 0.05 cm. Color — Greyed-green, nearest to RHS 195A. Ovary Color — Yellow-green, nearest to RHS 147A.

Seed and fruit: No fruit or seeds have been detected to date.

COMPARISONS WITH THE PARENT PLANTS AND MOST SIMILAR VARIETY OF COMMON KNOWLEDGE

Plants of the new cultivar 'RUYLAA1701' differ from its seed parent, *Lavandula angustifolia* 'Dwarf Blue' (not patented), by the characteristics described in Chart 1.

CHART 1

| Characteristic | 'RUYLAA1701' | 'Dwarf Blue' |
|---|---|---|
| Winter hardiness. | Not winter hardy. | Winter hardy. |
| Growth habit. | More compact than 'Dwarf Blue'. | Less compact than 'RUYLAA1701'. |
| Vernalization requirement. | No vernalization requirement. | Vernalization required. |

Plants of the new cultivar 'RUYLAA1701' differ from its pollen parent, an unnamed *Lavandula multifida* plant (not patented), by the characteristics described in Chart 2.

CHART 2

| Characteristic | 'RUYLAA1701' | The pollen parent. |
|---|---|---|
| Leaf shape. | Narrow oblanceolate; unlobed. | Double pinnate; deeply lobed. |
| Inflorescence. | Unbranched. | Branched. |
| Habit. | Perennial. | Short-lived; often an annual or biannual. |

Plants of the new cultivar 'RUYLAA1701' may be distinguished from its most similar known commercial comparator, *Lavandula pendunculata* 'IBPRU41016' (not patented in the United States; QZ application number 2017/0621), by the characteristics described in Chart 3.

CHART 3

| Characteristic | 'RUYLAA1701' | 'IBPRU41016' |
|---|---|---|
| Abundance of foliage. | Less abundant. | More abundant. |
| General coloration of the foliage. | Greyed-green. | Green. |

CHART 3-continued

| Characteristic | 'RUYLAA1701' | 'IBPRU41016' |
|---|---|---|
| Flower size. | Smaller than 'IBPRU41016'. | Larger than 'RUYLAA1701'. |
| General coloration of the flower. | Violet-blue, closer to blue. | Violet, closer to purple. |

That which is claimed is:

1. A new and distinct variety of *Lavandula angustifolia* plant named 'RUYLAA1701', substantially as described and illustrated herein.

* * * * *